United States Patent [19]

Stupay et al.

[11] 4,058,118
[45] Nov. 15, 1977

[54] PULSE COUNTER

[75] Inventors: Lawrence John Stupay, Endicott; Carl Frederick Truesdell, Johnson City, both of N.Y.

[73] Assignee: Bunker Ramo Corporation, Oak Brook, Ill.

[21] Appl. No.: 668,616

[22] Filed: Mar. 19, 1976

[51] Int. Cl.² .............................................. A61B 5/02
[52] U.S. Cl. ............................................. 128/2.05 T
[58] Field of Search .................. 128/2.05 P, 2.05 R, 128/2.05 T, 2.06 F, 2.06 R

[56] References Cited

U.S. PATENT DOCUMENTS

| | | | |
|---|---|---|---|
| 3,661,147 | 5/1972 | Mason | 128/2.05 T |
| 3,717,140 | 2/1973 | Greenwood | 128/2.05 T |
| 3,742,937 | 7/1973 | Manuel et al. | 128/2.05 T |
| 3,773,038 | 11/1973 | Smith et al. | 128/2.06 F |
| 3,807,388 | 4/1974 | Orr et al. | 128/2.05 P X |
| Re. 28,529 | 8/1975 | Edenhofer | 128/2.06 F |

*Primary Examiner*—Kyle L. Howell
*Attorney, Agent, or Firm*—William Lohff; F. M. Arbuckle; Richard Gray

[57] ABSTRACT

A miniaturized cardiotachometer is worn by a user typically adjacent the volar aspect of the wrist or the temple to provide the user with a numerical readout of his or her pulse rate. The time between two heartbeats is measured by the number of pulses from a fixed frequency source that occur. The measurement is made after a predetermined delay to eliminate or reduce noise signals, the number of pulses of the fixed frequency being converted into the pulse rate and displayed numerically.

15 Claims, 4 Drawing Figures

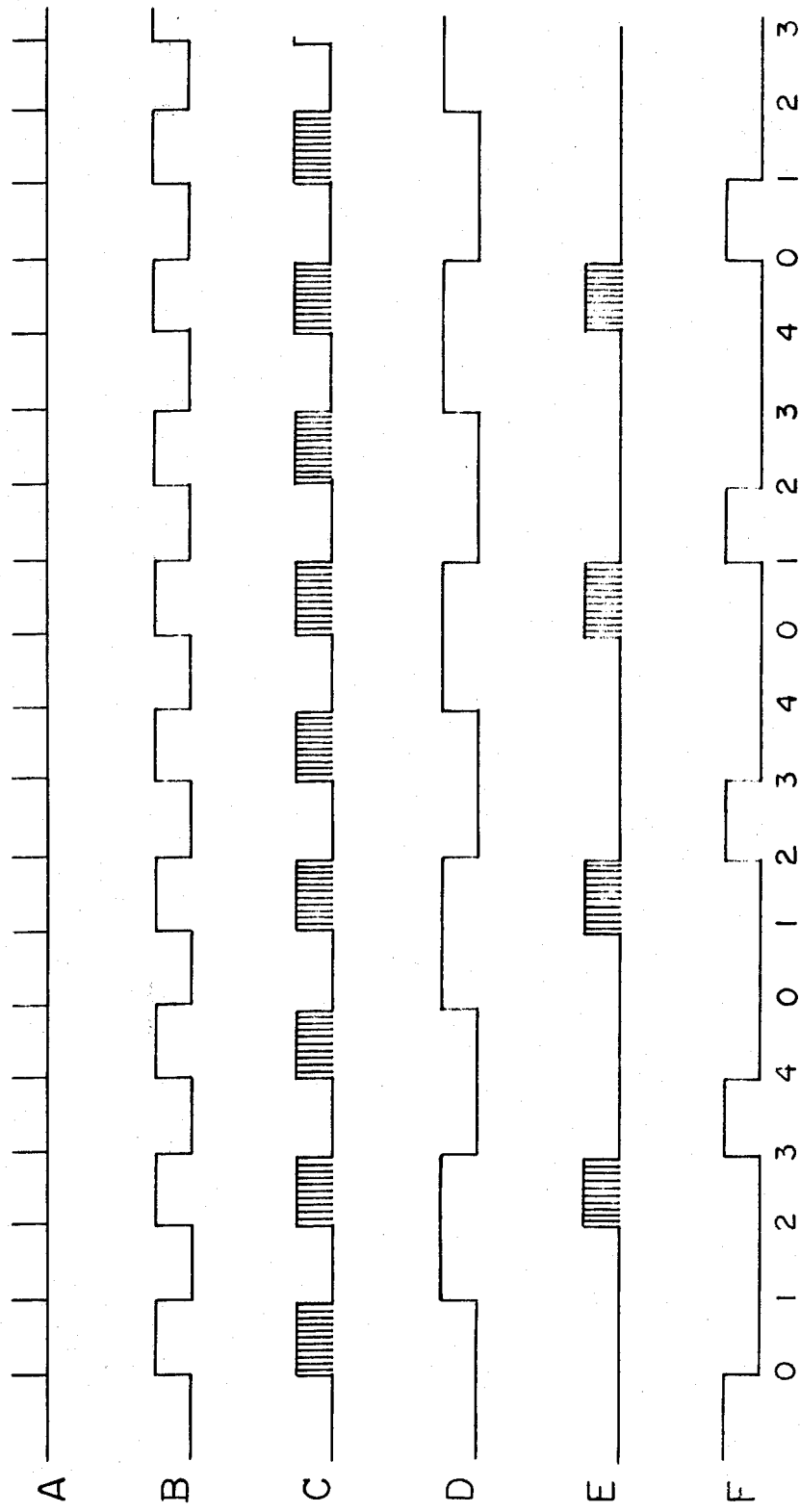

PULSE COUNTER

BACKGROUND OF THE INVENTION

1. Field of the Invention

The present invention relates to a cardiotachometer with visual readout and, more particularly, to a cardiotachometer that is worn by a user for determining the pulse rate based upon the time between two consecutive heartbeats after a predetermined delay and for immediately displaying the determined pulse rate numerically.

2. Description of the Prior Art

Heart rate is a basic parameter used to evaluate and determine the condition of the human body. It is for this reason that every patient in every hospital has his or her pulse taken at least once a day. The pulse rate is customarily determined by a nurse placing her fingers against the volar aspect of the wrist or the carotid artery of the neck and counting the number of beats per minute.

These beats per minute refer to the number of systoles per minute. A systolic heartbeat is that period in the functioning of the heart when it is contracting and forcing blood through the arteries in the course of which the arteries expand. This arterial expansion is that which is sensed through the nurse's fingers or by an appropriate transducer situated against the carotid artery or volar aspect, or any other well-known pressure point.

In the case of a transducer being applied to a pressure point, electrical impulses are produced which may be supplied to appropriate electronic circuitry for determining the systolic pulse rate. In the past, the electronic pulse rate measurement devices have required a relatively long time period to determine the pulse rate.

More recently, electronic pulse rate measurement devices have determined the pulse rate by measuring the time between two consecutive heartbeats. An undesirable feature of this procedure is that movements of the user are not distinguished from the systolic pulse by the transducer and thus false readings occur. To avoid such false readings, electronic pulse rate measuring devices have been designed to average the time intervals over ten or fifteen systolic heartbeats. The averaging technique results in a more accurate indication of pulse rate, but involves too much time for the measurement and error is averaged as well as the desired signals.

The present cardiotachometer utilizes miniaturized, solid state circuits, including a piezoelectric crystal as the pressure transducer to be placed against the volar aspect or the temple of the user. To eliminate the noise signals generated from movement by the patient, a present delay is incorporated during which time the patient must remain quiet to avoid noise input. Then an accurate reading is taken by measuring the time between two consecutive heartbeats.

SUMMARY OF THE INVENTION

In accordance with the present invention, there is provided a miniaturized cardiotachometer to be worn by a user for numerically indicating the user's pulse rate after the user has remained quiet for a few seconds. Typically, the device resembles a wrist watch with a piezoelectric transducer adjacent the volar aspect, having a numerical readout from a light-emitting-diode (LED) or liquid crystal display. The heart rate is determined, after an appropriate delay, by counting the number of fixed frequency pulses that occur between two heartbeats and then, through the use of appropriate electronic circuitry, converting the number of fixed frequency pulses into the pulse rate and displaying that rate in the LED or liquid crystal display.

Thus it is an object of the present invention to provide an improved cardiotachometer capable of providing a numerical indication of pulse rate with an extremely high degree of accuracy after a very short delay.

Another object of the present invention is to provide an apparatus capable of measuring pulse rate in a time interval between two consecutive heartbeats.

These and other objects will become apparent from a reading of the following detailed description of the preferred embodiment of the present invention.

BRIEF DESCRIPTION OF THE DRAWINGS

FIG. 4 shows representative waveforms (A–F) which may be utilized for gaining a complete understanding of the circuit operation of the preferred embodiment shown in FIG. 3.

DETAILED DESCRIPTION OF THE INVENTION

Figure 1:
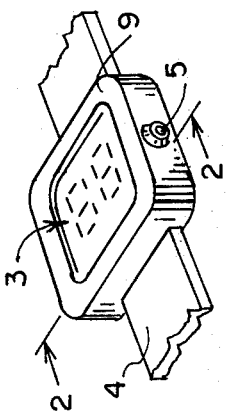
FIG. 1 is a perspective view of the invention embodied in a configuration similar to a wrist watch.

FIG. 1 illustrates a preferred embodiment 1 of the invention. A housing 9 contains an LED display 3, a button 5 for selectively activating the display and a wrist band 4 for holding the device against the wrist.

Figure 2:
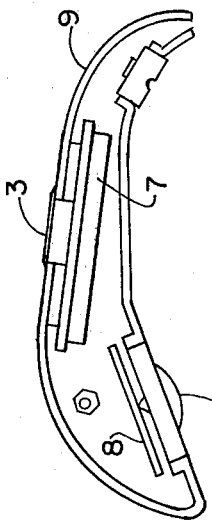
FIG. 2 is a cross-section of the invention shown in FIG. 1.

FIG. 2 is a cross-section of FIG. 1 showing an actuator 6 for contacting the volar aspect of the wrist. Actuator 6 is in contact with piezoelectric crystal 8 which provides an electrical impulse output upon pressure being exerted by actuator 6. An electronic package containing the required circuitry 7 is shown in place below LED unit 3.

It should be understood that although a wrist contacting device is shown as the preferred embodiment, a headband for contacting the user's temple is also contemplated as well as appropriate holding devices for other pressure points on a user's body.

Figure 3:
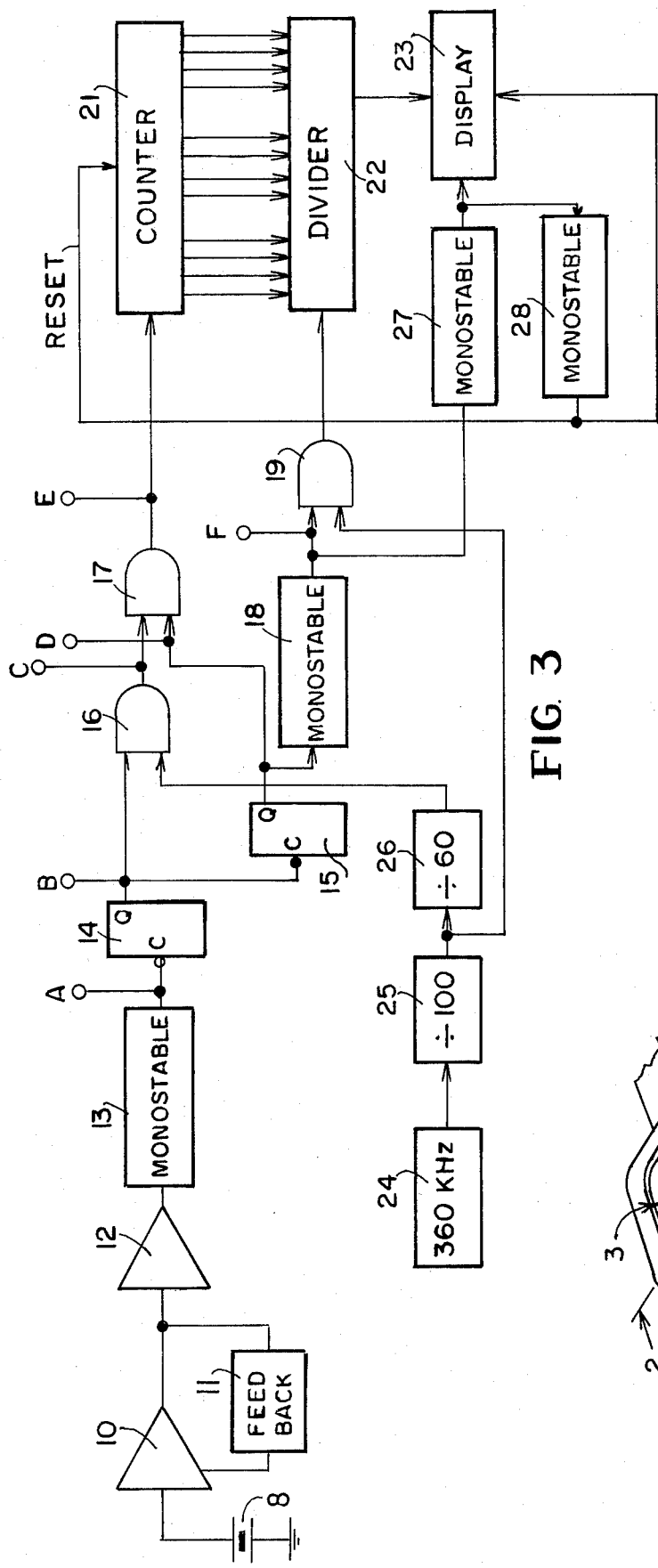
FIG. 3 is a block diagram of the electronic, logic circuits of the invention.

Referring now to FIG. 3, the entire system is shown in block diagram form. Piezoelectric crystal 8 is shown connected to operational amplifier 10 which has a feedback circuit 11 to provide an automatic gain control stage which serves as an input to operational amplifier 12. Operational amplifiers 10 and 12 are type SN72741, manufactured by Texas Instruments, Inc.

The output of amplifier 12 is shaped by monostable multivibrator 13 the output of which serves as the clock input to flip-flop 14 whose "Q" output serves as the clock input to flip-flop 15. Flip-flops 14 and 15 are circuit types SN7473 manufactured by Texas Instruments, Inc. The "Q" output of flip-flop 14 serves as one input to "AND" circuit 16 whose output serves as one input to "AND" circuit 17, the other input of which is provided by the "Q" output of flip-flop 15.

A 360 KHz clock 24 provides a constant frequency source and in this preferred embodiment is a well known, quartz crystal oscillator. A divider circuit 25 is connected to provide 3600 Hz and divider circuit 26 is connected to provide 60 Hz as the other input to "AND" circuit 16. Divider circuit 25 is formed by a cascade of three and divider 26 is formed by a cascade of two MC4016 Decade Counters, manufactured by Motorola. The "Q" output of flip-flop 15 also serves as a trigger to monostable multivibrator 18 which provides a one second activating pulse to "AND" circuit 19 whose other input is provided by divider 25. "AND" circuits 16, 17 and 19 are circuit types SN7408, manufactured by Texas Instruments, Inc.

The output of "AND" circuit 17 serves as an input to counter 21 which has a plurality of stages, specifically 12 stages in this preferred embodiment provided by cascading three type 8285 Binary Hexadecimal Synchronous up/down Counters, manufactured by Signetics.

The output of "AND" circuit 19 serves as a clock input to divider 22. The information inputs to divider 22 come from the stages of counter 21. Divider 22, in this preferred embodiment, has twelve stages and is formed by cascading three NC4018 Programmable 4-bit Binary down counters manufactured by Motorola.

The serial output of divider 22 provides an input to display unit 23. Display unit 23 is formed by a cascade of three circuit type TIL 307 NUMERIC DISPLAYS WITH LOGIC, manufactured by Texas Instruments, Inc.

The output of monostable multivibrator 18 also serves as an input to monostable multivibrator 27 whose output is used as a Strobe input to display unit 23 and also as an input to monostable multivibrator 28 whose output is used as a reset for display unit 23 and counter 21. Monostable multivibrators 13, 18, 27 and 28 are circuit types SN74121 manufactured by Texas Instruments, Inc.

The particular circuits identified above are, of course, exemplary only. It is contemplated that an integrated circuit chip having Complementary metal-oxide-silicon circuits (CMOS) or integrated current logic (T²L), or other FET circuits or other Bipolar circuits may be utilized as well in practicing the present invention. The specific circuit configurations could of course be altered from the preferred embodiment shown herein but would not depart from the spirit of this invention.

MODE OF OPERATION

The systolic pulses are detected and transduced into electric signals which are amplified by amplifiers 10 and 12 and then formed into binary signals by monostable multivibrator 13, all as shown in FIG. 3. Waveform A is the output of monostable multivibrator 13 and is shown in FIG. 4 where each single pulse is indicative of a systolic pulse detected by the transducer. The pulses of waveform A trigger flip-flop 14 on their negative-going edges and provide an output waveform B shown in FIG. 4 as being a positive pulse of a time duration of the period between every other pair of pulses of waveform A. Waveform B modulates a 60 Hz square wave (not shown) from frequency divider 26 through "AND" circuit 16 providing an output waveform C. It is to be noted that waveform C represents discrete envelopes of 60 Hz pulses, the number of 60 Hz pulses being determined by the time between heartbeats as indicated in waveform B. For example, if a normal, male heart rate is assumed to be 72 beats per minute, the time period between heartbeats is 5/6 seconds. In 5/6 seconds, fifty 60 Hz pulses are enveloped.

The other flip-flop 15, which is triggered by flip-flop 14 has an output which is half the frequency of flip-flop 14 as shown in waveform B, forming a two stage counter. Waveforms C and D result in waveform E by action of "AND" circuit 17. By this combination, it is readily seen that the envelopes of 60 Hz pulses occur for every fourth heartbeat of waveform A. This arrangement provides a time period during which the user remains quiet to avoid noise signal entry into the system. In the example given, the fifty of the 60 Hz pulses are transmitted to and counted by counter 21.

Flip-flop 15 provides a trigger on the negative-going edge of the signal to monostable multivibrator 18 which provides, by reason of the selected parameters, a one second output waveform F. Waveform F is initiated following the count by counter 21. The output of frequency divider 25 provides 3600 Hz (not shown) which output is modulated by waveform F in "AND" circuit 19 providing a series of 3600 pulses into divider 22. The dividing is done in a well known manner by transmitting the count of counter 21 to the divider 22 and then counting down the transmitted number to zero by subtracting each of the 3600 pulses coming in from "AND" circuit 19. When divider 22 counts to zero, a single pulse is sent to display unit 23. The number of times that divider 22 is counted down to zero is 3600 divided by the number transmitted from counter 21. In the example, 3600 divided by 50 equals 72 which is the number of heartbeats per minute. Each time divider 22 is counted to zero, a pulse is transmitted to a counter in display unit 23. In the example given, the number 72 is held in that counter in appropriate format for activating the light-emitting-diode portion of display unit 23.

Some time after the number to be displayed is entered in the counter portion of display unit 23, a Strobe signal is sent from monostable multivibrator 27, the time being determined by parameters of that multivibrator. The Strobe signal activates the display unit logic and permits the number stored in the counter portion to be displayed in the LED portion 3 as shown in FIGS. 1 and 2. After a predetermined time, the display is reset as is counter 21 by multivibrator 28.

Those skilled in the art will recognize that the delay shown in waveform E can be varied using various techniques. For example, another flip-flop could be added or a larger counter with appropriate logic could be used to obtain the desired time delay. There are many other forms of well known delay circuits that could be employed as well.

Likewise, those skilled in the art realize that the translation of the enveloped 60 Hz pulses can be accomplished in various ways. For example, a circuit without a pulse entry for dividing 3600 by the number of enveloped 60 Hz pulses could be employed. Also, a read-only-memory (ROM) could be employed where the number of enveloped 60 Hz pulses serves as an address where the number stored at the address is the corresponding number of heartbeats. For example, at address 50, the number 72 would be found. Also, other frequencies may be used.

The use of circuitry not shown specifically herein and of logic designed to achieve the same results are all contemplated by the breadth and scope of this invention.

We claim:
1. A cardiotachometer adapted to be attached to a living body and for providing an accurate indication of the heart beat rate of the living body, comprising:
 a. heart beat detection means for detecting each heart beat and for providing a discrete electrical pulse for each heart beat, wherein the time between im- mediately successive discrete electrical pulses represent heart beat intervals;

b. means for holding said detection means against the body at a point where a heart beat can be detected;

c. first pulse generating means for providing a series of first electric pulses at a first rate;

d. first heart beat interval select means coupled to said detection means for selecting a first set of heart beat intervals comprising certain ones of said heart beat intervals;

e. first gate means coupled to said first heart beat interval select means and to said first pulse generating means and having an output for gating to said output the number of said first pulses occurring during each of said first set of intervals, said number of gated first pulses representing the heart beat rate in pulses per heart beat interval;

f. a counter;

g. second heart beat interval select means coupled to said first heart beat interval select means for selecting certain ones of said first set heart beat intervals, h. second gate means coupled to said first gate means output and to said second heart beat interval select means and having an output coupled to said counter for gating said first pulses occurring during each of said selected first set intervals into said counter;

i. second pulse generating means for providing a series of second electric pulses at a second rate;

j. third gate means coupled to said second pulse generating means and having an output for gating a given number of said second pulses to said output during a predetermined time interval;

k. divider means coupled to said counter and to said third gate means output for dividing said given number of said second pulses by the number of said first pulses occurring during one of said selected first set heart beat intervals to thereby provide an output indicative of the heart beat rate of the living body; and l. display means coupled to said divider means for displaying the heart beat rate of the living body.

2. The cardiotachometer of claim 1 wherein said heart beat detection means comprises a piezoelectric crystal for converting said heart beats into discrete electrical impulses.

3. The cardiotachometer of claim 1 wherein said second pulse generating means comprises a first pulse generator and a first frequency divider.

4. The cardiotachometer of claim 3 wherein said second pulse rate is 3600 Hz.

5. The cardiotachometer of claim 3 wherein said first pulse generating means comprises a second frequency divider coupled to said first frequency divider.

6. The cardiotachometer of of claim 5 wherein said first pulse rate is 60 Hz.

7. The cardiotachometer of claim 1 wherein said first heart beat interval select means comprises a first flip-flop having a clock input coupled to said detection means and an output coupled to said first gate means whereby said first set of heart beat intervals comprises every other one of said heart beat intervals.

8. The cardiotachometer of claim 7 wherein said first gate means comprises a first and gate having a first input coupled to said first flip-flop output and a second input coupled to said first pulse generating means.

9. The cardiotachometer of claim 8 wherein said second heart beat interval select means comprises a second flip-flop having a clock input coupled to said first flip-flop output and an output coupled said second gate means to thereby select every other one of said first set of heart beat intervals.

10. The cardiotachometer of claim 9 wherein said second gate means comprises a second and gate having a first input coupled to said second flip-flop output and a second input coupled to said first gate means.

11. The cardiotachometer of claim 9 wherein said third gate means comprises a monostable multivibrator and a third and gate, said monostable multivibrator having an input coupled to said second flip-flop output and an output, said third and gate having a first input coupled to said monostable multivibrator output, a second input coupled to said second pulse generating means, and an output coupled to said divider means.

12. The cardiotachometer of claim 11 wherein said third gate means gates said second pulses for a predetermined time interval of one second.

13. The cardiotachometer of claim 12 wherein said second rate is 3600 Hz whereby said third gate means gates 3600 pulses into said divider means.

14. The cardiotachometer of claim 1 further comprising reset means for resetting and display means and said counter.

15. The cardiotachometer of claim 14 wherein said reset means comprises a monostable multivibrator coupled to said display means and to said counter for resetting said display means and said counter after the heart beat rate has been displayed for a predetermined period of time.

* * * * *